United States Patent [19]

Sun et al.

[11] Patent Number: 5,270,200
[45] Date of Patent: Dec. 14, 1993

[54] ARCELIN SEED STORAGE PROTEINS FROM PHASEOLUS VULGARIS

[75] Inventors: Samuel S. M. Sun, Honolulu, Hi.; Thomas C. Osborn, Madison, Wis.

[73] Assignee: The Plant Cell Research Institute, Dublin, Calif.

[21] Appl. No.: 595,792

[22] Filed: Oct. 9, 1990

Related U.S. Application Data

[63] Continuation of Ser. No. 180,404, Apr. 12, 1988, abandoned.

[51] Int. Cl.$^5$ .................... C12N 5/04; C12N 15/29; C12N 15/82
[52] U.S. Cl. .................. 435/240.2; 435/172.3; 435/252.3; 435/317.1; 435/320.1; 530/370; 530/396; 536/23.6; 800/205; 800/DIG. 23; 800/DIG. 70; 935/64; 935/67; 504/116; 504/117; 504/100; 47/57.6
[58] Field of Search .................. 435/172.3, 320, 317.1, 435/240.4; 800/1, 205; 530/396; 536/23.6

[56] References Cited

U.S. PATENT DOCUMENTS 4,407,956 10/1983 Howell .................... 935/25
4,771,002  9/1988 Gelvin .................... 435/253

FOREIGN PATENT DOCUMENTS 0122791 10/1984 European Pat. Off. .
0126546 11/1984 European Pat. Off. .

OTHER PUBLICATIONS

Osborn et al., 1988, Science 240:207–210 (8 Apr. 1988).
Osborn et al., 1988, Plant Physiol. 86:399–405.
Bliss, F. A., 1987, (Dec.) Project No. WIS01626 Progress Report 87-01 to 87-12; CRIS DATABASE.
Bliss, F. A., 1986, (Dec.) Project No. WIS-8100050 Progress Report 86-01 to 86-12; CRIS DATABASE.
Osborn et al., 1986, Theor. Appl. Genet. 71:847–855.
Romero Andreas et al., 1986, Theor. Appl. Genet. 72:123–128.
Hoffman et al., 1985, EMBO J 4:883–889.
Harmsen et al., 1988, Ann. Report of Bean Improvement Cooperative 31:54–55.
Schoonhoven et al., J. Econ. Entomol. (1983) 76:1255–1259.
Murai et al., Science (1984) 222:476–482.
Segupta-Gopalan et al., Proc. Natl. Acad. Sci. (1985) 82:3320–3324.
Matzke et al., EMBO J. (1984) 3:1525–1531.
Messing, Genet. Engineering (1987) W. U. Rigby editor, Academic Press, 6:1–46.

Primary Examiner—David T. Fox
Assistant Examiner—P. R. Moody
Attorney, Agent, or Firm—Morrison & Foerster

[57] ABSTRACT

Nucleic acid sequences encoding the *Phaseolus vulgaris* storage protein arcelin-1 are provided. These sequences are useful in providing transformed plant cells and plants which are insect-resistant.

17 Claims, 2 Drawing Sheets

1  C₁₂ATGAATGCATAC ATG GCT TCC TCC AAC TTA CTC ACC CTA GCC CTC TTC CTT GTG 66
               MET Ala Ser Ser Asn Leu Leu Thr Leu Ala Leu Phe Leu Val

67  CTT CTC ACC CAC GCA AAC TCA AGC AAC GAC GCC TCC TTC AAC GTC GAG ACG TTC 120
    Leu Leu Thr His Ala Asn Ser Ser Asn Asp Ala Ser Phe Asn Val Glu Thr Phe

121 AAC AAA ACC AAC CTC ATC CTC CAA GGC GAT GCC ACC GTC TCA TCC GAA GGC CAC 172
    Asn Lys Thr Asn Leu Ile Leu Gln Gly Asp Ala Thr Val Ser Ser Glu Gly His

173 TTA CTA CTA ACC AAT GTT AAA GGC AAC GAA GAG GAC TCT ATG GGC CGC GCC TTC 228
    Leu Leu Leu Thr Asn Val Lys Gly Asn Glu Glu Asp Ser Met Gly Arg Ala Phe

229 TAC TCC GCC CCC ATC CAA ATC AAT GAC AGA ACC ATC GAC AAC CTC GCC AGC TTC 282
    Tyr Ser Ala Pro Ile Gln Ile Asn Asp Arg Thr Ile Asp Asn Leu Ala Ser Phe

283 TCC ACC AAC TTC ACA TTC CGT ATC AAC GCT AAG AAC ATT GAA AAT TCC GCC TAT 336
    Ser Thr Asn Phe Thr Phe Arg Ile Asn Ala Lys Asn Ile Glu Asn Ser Ala Tyr

337 GGC CTT GCC TTT GCT CTC GTC CCC GTC GGC TCT CGG CCC AAA CTT AAA GGC CGT 390
    Gly Leu Ala Phe Ala Leu Val Pro Val Gly Ser Arg Pro Lys Leu Lys Gly Arg

391 TAT CTA GGT CTT TTC AAC ACA ACC AAC TAT GAC CGC GAC GCC CAT ACT GTG GCT 444
    Tyr Leu Gly Leu Phe Asn Thr Thr Asn Tyr Asp Arg Asp Ala His Thr Val Ala

445 GTG GTG TTC GAC ACC GTC AGC AAC CGT ATT GAA ATC GAC GTG AAC TCC ATC CGG 498
    Val Val Phe Asp Thr Val Ser Asn Arg Ile Glu Ile Asp Val Asn Ser Ile Arg

499 CCT ATC GCA ACG GAG TCT TGC AAT TTC GGC CAC AAC AAC GGA GAA AAG GCC GAG 552
    Pro Ile Ala Thr Glu Ser Cys Asn Phe Gly His Asn Asn Gly Glu Lys Ala Glu

553 GTT CGG ATC ACC TAT GAC TCC CCC AAG AAC GAC TTG AGG GTT TCT CTG CTT TAC 606
    Val Arg Ile Thr Tyr Asp Ser Pro Lys Asn Asp Leu Arg Val Ser Leu Leu Tyr

607 CCT TCT TCG GAA GAA AAG TGC CAC GTC TCT GCC ACA GTG CCG CTG GAG AAA GAA 660
    Pro Ser Ser Glu Glu Lys Cys His Val Ser Ala Thr Val Pro Leu Glu Lys Glu

661 GTT GAG GAC TGG GTG AGC GTT GGG TTC TCT GCC ACC TCA GGG TCG AAA AAA GAG 714
    Val Glu Asp Trp Val Ser Val Gly Phe Ser Ala Thr Ser Gly Ser Lys Lys Glu

715 ACC ACT GAA ACG CAC AAC GTC CTC TCT TGG TCT TTT TCT TCC AAC TTC ATC AAT 768
    Thr Thr Glu Thr His Asn Val Leu Ser Trp Ser Phe Ser Ser Asn Phe Ile Asn

768 TTT AAG GGC AAA AAA TCT GAA CGT TCC AAC ATC CTC CTC AAC AAG ATC CTC TAG 822
    Phe Lys Gly Lys Lys Ser Glu Arg Ser Asn Ile Leu Leu Asn Lys Ile Leu  ·

823 ACTCCCAAAGCCAGCTTCACTGTGACAGTAAAACCTTCCTTATACGCTAATAATGTTCATCTGTCACACAA 893

894 ACTCCAATAAATAAAATGGGAGCAATAAATAAAATGGGAGCTCATATATTTACAC                948

FIG. I

```
  1 MASSNllslaLFLVLLTHANSasqtsFsFQRFNETNLILQRDAtVSSKGQLRLTNVNdNGEPtlsSLGRAFY
    |||| ||||||||||||||||  ||| ||||||||||||||||||| |||||||| |||||| ||||||||
  1 MASS kfftvLFLVLLTHANSSNDiyFNFQRFNETNLILQRDAsVSSsGQLRLTNiNGNGEPrvgSLGRAFY
    |||||| |||||||||||||| ||  |||||||||||||||| |||||||||||  ||| ||  |||||||
  1 MASSnLLtLALFLVLLTHANSSNDaSFNvetFNKTNLILQGDATVSSeghLlLTNvKGN   eeDSMGRAFY
    |||| || ||| ||| |||||                                         |  ||||||
  1 MASSkLLsLALFLaLLsHANSatetSFiidaFNKTNLILQGDATVSS       ngnlqlsynsyDSMsRAFY 73 SAPIQIWDNTTGaVAaspTSFTFNIdVPNNsGPADGLAFVLIPVGSQPKDKGG1LGLFnnykydSNaHTVAV
    ||||||||||||| ||  ||||||| ||| |||||||||| ||||||||||| ||||       |||||||
 72 SAPIQIWDNTTGtVASFaTSFTFNIqVPNNaGPADGLAFALVPVGSQPKDKGGfLGLF   dgsnSNfHTVAV
    |||||      |     ||||| ||     |||||||| |||||| |||||  ||
 70 SAPIQInDrTidNIASFsTNFTFrInakNieNSAyGLAFALVPVGSrPK1KGryLGLFnttnydrdaHTVAV
    ||||| |                                                             |  |
 67 SAPIQIrDsTtgNvASFdTNFTmnIrthrqaNSAVgLdFvLVPV   qPesKG              dTVtV 145 EFDTLYNvhWDPkpRHIGIDVNSI   ksIKTTtwDFVkGENAEVLITYDSSTkLLVASLVYPSIKTSFIVSD
    ||||||| ||||  ||||||||||    ||||| |||| ||||||||||||| ||||||||||  ||||||
142 EFDTLYNkdWDPteRHIGIDVNSIR   SIKTTrwDFVnGENAEVLITYDSSTNLLVASLVYPSqkTSFIVSD
    ||||
142 vFDT              vsnRIeIDVNSIRpIatescnfghnNGEkAEVRITYDpkNdLrvSLIYPSseekchVSa
    |||                                         | ||||||||    | |||||||
122 eFDT               flsRIsIDVN nndIksvpwdvhdydGqnAEVRITYnSstkvfsVSLsnpSTgksnnVST 215 TVDLKSVLPEWVIvGFtATTGItKGNVETNDiLSWSFASKLSDGTTSEalNLNANFalNqIL.
    |||||||||||| ||| |||||||||||||| ||||||||||||||| ||||||| || |||
212 TVDLKSVLPEWVSVGFSATTGInKGNVETNDVLSWSFASKLSDGTTSEglNLNANIvLNKIL.
                     ||| ||   |||||  |||||              ||||| ||||
206 TVpLEKEVeDWVSVGFSATSGskKettEThnVLSWSF SSNFINFKgkKSERSNIiLNKIL.
    || |||| |||||||||||||      |  |||||| |||||| |  ||||||| ||||||
185 TVeLEKEVyDWVSVGFSATSGayqwsyEThdVLSWSF SSNFINiKdqKSERSNIvLNKIL.
```

FIG. 2

ARCELIN SEED STORAGE PROTEINS FROM PHASEOLUS VULGARIS

This application is a continuation of application Ser. No. 07/180,404, filed Apr. 12, 1988, now abandoned.

TECHNICAL FIELD

The present invention is directed to plants and plant proteins. More particularly, the present invention is directed to arcelin seed storage proteins from the *Phaseolus vulgaris*, nucleic acid sequences encoding such proteins, and the use of such nucleic acid sequences.

BACKGROUND

There are two commonly known seed storage proteins in the cultivated common bean, *Phaseolus vulqaris*: phytohemagglutinin (PHA, also referred to as bean lectin) and phaseolin. Recently, wild forms of *Phaseolus vulqaris* L., indigenous to Middle and South America, have been found to contain a novel family of proteins previously unreported in the common bean. These proteins, named arcelins, have subunit molecular weights similar to lectin proteins or intermediate to phaseolin and lectin proteins, and occur in the globulin-2 protein fraction. Four electrophoretic variants, or isoproteins, have been observed and designated arcelin-1, -2, -3 and -4. See Romero Andreas et al. (1986) *Theor Appl. Genet.* 72:123-128; Osborn et al. (1986) *Theor. Appl. Genet.* 71:847-855.

The presence of arcelin in wild beans has been correlated with resistance to two bruchid beetle species. It is not known, however, whether this resistance is attributable to arcelin in whole, or even in part. See Osborn et al. supra; Schoonhoven et al. (1983) *J. Econ. Entomol.* 76:1255-1259.

Other seed storage proteins have been cloned and expressed in heterologous plants. For example, a sample for phaseolin protein from *Phaseolus vulgaris* (French bean) has been cloned and expressed in heterologous plants under the control of its own promoter and heterologous promoters. See, e.g., Murai et al. (1984) Science 222:476; Segupta-Gopalan et al. (1985) Proc. Natl. Acad. Sci, USA 82:3320; EPO Pub. No. 126,546; EPO Pub. No. 122,791. Heterologous plants have also been transformed by the gene for the corn storage protein, zein. Matzke et al. (1984) *EMBO J.* 3:1525-1531; Messing in *Genetic Engineering* 6:1-46 (W. J. Rigby ed. 1987). The Brazil nut 2S storage protein has also been expressed in heterologous plants. See copending U.S. Pat. App. Ser. No. 065,303, filed Jun. 19, 1987.

SUMMARY OF THE INVENTION

The present invention provides nucleic acid sequences, particularly DNA sequences, encoding arcelin. It has also been determined that the arcelin proteins alone are toxic to bean bruchid pests, and the transfer of the gene encoding arcelin to bean cultivars results in insect resistance. Thus, the present invention provides nucleic acid sequences which are useful in the genetic transformation of plants to improve nutritional value and to introduce insect resistance.

BRIEF DESCRIPTION OF THE FIGURES

FIG. 1 shows the nucleotide sequence and derived amino acid sequence of an arcelin cDNA (arcelin-1) from plasmid pAR1-11. The 265 amino acid open reading frame is shown. The third ATG is presumed to be the initiation codon. The mature protein N-terminal sequence, as determined by Edman degradation, is underscored.

FIG. 2 shows a comparison of the nucleotide-derived amino acid sequences of PHA-L (first line, Hoffman et al., 1985, *EMBO J* 4:883), PHA-E (second line, id.), arcelin-1 (third line) and a "lectin-like" protein (fourth line, Hoffman et al., 1982, *Nucl. Acids Res.* 10:7819).

DETAILED DESCRIPTION OF THE INVENTION

In addition to the techniques described below, the practice of the present invention will employ conventional techniques of molecular biology, microbiology, recombinant DNA technology, and plant science, all of which are within the skill of the art. Such techniques are explained fully in the literature. See, e.g., Maniatis et al., *Molecular Cloning: A Laboratory Manual* (1982); *DNA Cloning*: Volumes I and II (D. N. Glover ed. 1985); *Oligonucleotide Synthesis* (M. J. Gait ed. 1984); *Nucleic Acid Hybridization* (B. D. Hames & S. J. Higgins eds. 1985); *Transcription and Translation* (B. D. Hames & S. J. Higgins eds. 1984); *Animal Cell Culture* (R. I. Freshney ed. 1986); *Plant Cell Culture* (R. A. Dixon ed. 1985); *Propagation of Higher Plants Through Tissue Culture* (K. W. Hughes et al. eds. 1978); *Cell Culture and Somatic Cell Genetics of Plants* (I. K. Vasil ed. 1984); Fraley et al. (1986) CRC Critical Reviews in Plant Sciences 4:1 (hereinafter *Plant Sciences*); *Biotechnology in Agricultural Chemistry: ACS Symposium Series* 334 (LeBaron et al. eds. 1987); *Genetic Engineering*, Vol. 6 (Rigby ed., 1987).

In describing the present invention, the following terminology will be used in accordance with the definitions below.

A "replicon" is any genetic element (e.g., plasmid, cosmid, chromosome, virus, etc.) that behaves as an autonomous unit of DNA replication in vivo; i.e., capable of replication under its own control within a cell.

A "vector" is a replicon, such as a plasmid, cosmid, or bacteriophage, to which another DNA segment may be attached so as to bring about replication of the attached segment, or to allow its introduction into a cellular host.

A "DNA molecule" refers to the polymeric form of deoxyribonucleotides (adenine, guanine, thymine, or cytosine) in either single- or double-stranded form. The double-stranded form may, of course, be implied by the context of the molecule's environment (e.g., a chromosome). When in the double-stranded form, the molecule will usually be in its normal, double-stranded helix. The term "DNA molecule" is not limited to any particular tertiary form of DNA. Thus, the term includes double-stranded DNA found, inter alia, in linear DNA molecules, viruses, plasmids, and chromosomes. When discussing the structure of particular double-stranded DNA molecules, sequences may be described herein according to the normal convention of giving only the sequence in the 5' to 3' direction (left to right) along the nontranscribed (anti-sense) strand of DNA (i.e., the strand having a sequence homologous to the mRNA). If both strands are shown, the anti-sense strand will be on top.

A DNA "coding sequence" is a DNA sequence which is transcribed and translated into a polypeptide in vivo when placed under the control of appropriate regulatory sequences. The boundaries of the coding sequence are determined by the start codon at the 5' terminus and a translation stop codon at the 3' terminus. Examples of coding sequences include cDNA reverse transcribed from eukaryotic mRNA, genomic DNA sequences from eukaryotic cells, and synthetic DNA sequences.

A cell which has been "transformed" by an exogenous DNA sequence is a cell into which the exogenous DNA has been introduced. The exogenous DNA may be integrated (covalently linked) to chromosomal DNA making up the genome of the cell, or it may remain extrachromosomal. "Stably" integrated DNA sequences are those which are inherited through chromosome replication by daughter cells or organisms (accounting for loss by Mendelian segregation). This stability is exhibited by the ability to establish cell lines or clones comprised of a population containing the exogenous DNA.

A "clone" or "cell line" is a population of cells descended from a single cell or common ancestor by mitosis and is capable of stable growth in vitro for many generations.

A composition of a first type of matter (e.g., a DNA molecule containing a coding region) is "substantially free" of a second type of matter (e.g., DNA molecules which do not contain a coding region) if the composition is comprised of less than about 10% (weight/weight) of the second type of matter relative to the sum of the first and second types of matter. Preferably, the composition contains less than about 5% of the second type of matter, most preferably less than about 1%.

Two sequences, such as nucleic acid sequences or amino acid sequences, are "substantially homologous" when the sequences are a minimum of about 90% homologous over a selected region, and preferably at least about 95% homologous.

The various isoforms of arcelin characterized to date from wild bean accessions have been shown in 2-dimensional electrophoretic analysis to have molecular weights ranging from 35,000 to 42,000, and a more basic isoelectric points than phaseolin. See, e.g., Osborn et al. (1986) supra; Romero Andreas et al. (1986) supra. Arcelin occurs in the globulin-2 protein fraction, and it is controlled genetically in a simple Mendelian fashion. The expression of alleles for the presence of different arcelin variants is codominant with respect to each other, and dominant with respect to alleles for the absence of arcelin. Genes controlling arcelin expression are also tightly linked to those controlling PHA expression. Arcelins may also be characterized by shared epitopes that do not appear on PHA or lectins.

As an illustrative example, arcelin-1 has been further characterized, as more fully described in the examples below. During purification, arcelin-1 behaved both as an albumin and globulin seed protein. In fact, arcelin-1 initially occurred in the globulin-a fraction and later partitioned into albumin-b and globulin-b fractions. These results contrast with those of Romero Andreas et al., supra, who reported that arcelin behaved as a globulin protein. PHA, however, has also been shown to occur in both albumin and globulin protein fractions; PHA also co-purified with arcelin in the albumin-b fraction in the experiments reported below. Arcelin-1, unlike PHA, did not bind to Sepharose ®-thyroglobulin or Sepharose ®-fetuin affinity resins.

The subunit molecular weights of arcelin-1 and PHA were very similar, and their deglycosylated molecular weights were almost identical. Most of the arcelin-1 protein had a molecular weight corresponding to a dimeric form. A small amount of a tetrameric form, however, was also observed. As previously reported, it was confirmed that arcelin-1 has a more basic isoelectric point than PHA. Although arcelin-1 and PHA have a similar amino acid composition, arcelin-1 has more basic amino acids (lysine, histidine, and arginine). While mature PHA does not contain methionine, arcelin-1 contains at least one methionine residue. While there is some immunocross-reactivity between PHA and arcelin-1, the latter does not have the usual hemagglutinating activity observed for PHA. Arcelin-1, however, did react with some receptors that are exposed when some erythrocytes are treated with pronase.

The arcelin-1 coding sequences and amino acid sequences are highly homologous with two genes encoding PHA. FIG. 1 shows arcelin-1 encoding cDNA and its deduced amino acid sequence. There is approximately 78% nucleic acid homology between the protein coding sequences of pARl-11, and each of the PHA genes, pdlec1 and pdlec2. Hoffman et al. (1985) *EMBO J* 4:883. A cDNA clone encoding a lectin-like protein shows an 81% nucleic acid homology to the pARl-11 coding sequence. The derived amino acid sequence of arcelin-1 is 58% to 61% homologous to the derived amino acid sequences of these other lectin clones. See FIG. 2.

Bean lines with arcelin-1 have high levels of resistance to *Z. subfasciatus,* and low levels of resistance to *A. obtectus.* The opposite is true with bean lines expressing arcelin-2, and lines with arcelin-4 have high levels of resistance to both species. Arcelins, however, appear to be safe for mammals. Preliminary studies indicate that arcelin (e.g., arcelin-1) has no adverse effects on rat growth and metabolism when ingested as diet of cooked beans.

In accordance with the present invention, a DNA molecule is provided which contains a coding region that encodes an arcelin seed storage protein of *P. vulgaris*. The DNA molecules can encode either a genomic or cDNA sequence, and either a complete presequence, or a mature sequence. DNA molecules according to the present invention can be comprised of a coding region which is entirely homologous to native DNA; e.g., cDNA or genomic DNA. Alternatively, the coding region can be partially or completely synthetic in nature; e.g., comprised of codons different than that found in the native plant, yet encoding substantially the same protein. This may be particularly preferred when it is intended to express the coding region in a heterologous host, thereby allowing for the selection of host-preferred codons. See, e.g., U.S. Pat. No. 4,356,270; EPO Pub. No. 46,039.

In a preferred embodiment of the present invention, the DNA sequences encoding arcelin will be "flanked by DNA sequences heterologous" to the arcelin coding sequences. This means that the coding sequences flanked at both the 5' and 3' ends by DNA which is not found in the comparable flanking positions in the *P. vulgaris* wild-type genome. Examples of DNA constructs falling within this definition include plasmids carrying arcelin-encoding sequences, linear DNA sequences containing non-*P. vulgaris* DNA in the 5' and 3' positions, or a *P. vulgaris* chromosome transformed with an arcelin-encoding sequence that integrates at a position other than the location of the wild-type gene. Particularly preferred flanking, heterologous sequences are those elements which make up the expression cassettes described below.

DNA molecules encoding arcelin can be prepared synthetically by known methods of oligonucleotide synthesis. Synthetic coding sequences can be prepared from overlapping oligonucleotides whose sequence contain codons for the amino acid sequence of the storage protein. Such oligonucleotides are prepared by standard methods and assembled into a complete coding sequence. See, e.g., Edge (1981) Nature 291:756; Nambiar et al. (1984) Science 323:1299; Jay et al. (1984) J. Biol. Chem. 259:6311; *Oligonucleotide Synthesis* (supra).

Arcelin coding sequences can also be isolated employing methods of screening cDNA or genomic libraries. While short probes can be prepared from the nucleic acid sequences disclosed herein, it is preferred to employ the entire coding sequences disclosed herein as a probe when screening libraries for other variants. Due to the homology between the variants, isolation of additional DNA sequences encoding different isoproteins is within the skill of the art by employing the nucleic acid sequences disclosed herein as probes. See, e.g., *Molecular Cloning: A Labratory Manual* (supra); *DNA Cloning: Vol. I & II* (supra); *Nucleic Acid Hybridization* (supra).

The synthesis or isolation of DNA molecules containing the described coding sequences permits those of skill in the art to prepare compositions of DNA molecules encoding arcelin substantially free of DNA molecules which do not encode the storage protein. The compositions of DNA molecules containing coding sequence according to the present invention can be comprised of linear coding sequences, or coding sequences in cloning vectors. Numerous cloning vectors are known to those skilled in the art, and the selection of an appropriate cloning vector is a matter of choice. Examples of recombinant DNA vectors for cloning in the host cells which they transform include bacteriophage lambda (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (bacillus), pIJ61 (Streptomyces), pUC6 (Streptomyces), actinophage phi C31 (Streptomyces), YIp5 (yeast), YCp19 (yeast), and bovine papilloma virus (mammalian cells). See, qenerally, *DNA Cloning: Volumes I & II* (supra); *Molecular Cloning: A Laboratory Manual* (supra).

In accordance with the present invention, DNA constructs are provided in which the above-described coding sequences are placed under the control of transcription regulatory sequences so that the arcelin storage protein is expressed in a host cell. Such DNA constructs, referred to as "expression cassettes", are comprised of the storage protein coding sequence under the control of regulatory sequences, such as a promoter, ribosome binding site (for bacterial expression) and a transcription termination sequence or polyadenylation signal. Other regulatory sequences include operators, enhancers, and the like. The cassette is usually flanked by convenient restriction sites. The selection of the appropriate regulatory sequence and coding sequence, as well as their assembly for expression in a particular host, is within the skill of the art.

It is usually desirable to include within the expression cassette a selectable marker. A "selectable marker" gene encodes a "selectable phenotype"; i.e., a phenotype of a cell or organism which allows for the identification or selection of cells expressing the selectable marker gene. Well-known marker genes are known in the art, including, but not limited to, the gene for chloramphenicol acetyltransferase (CAT), neomycin phosphotransferase (neo$^5$), neomycin phosphotransferase II (npt-II), nopaline synthase (NOS), hygromycin phosphotransferase, the glyphosate resistance gene (EPSP), dihydrofolate reductase (mtx$^R$), hypoxanthine phosphoribosyltransferase (hpt), and thymidine kinase (tk). Cells transformed with sequences encoding these proteins are able to survive on media which would otherwise be toxic to the cell. Other types of markers, such as beta-galactosidase (lacZ) cause cells transformed therewith to change color under certain conditions, thus allowing for visual selection. The presence of the selectable marker in the expression cassette allows for the determination of whether a particular cell has been transformed stably by the expression cassette. Selectable markers can be included which function in the ultimate host which will express the storage protein, as well as additional markers which will function in intermediate hosts in which the construction of the expression cassette occurs.

The expression cassette is constructed so that the coding sequence is located within the cassette with the appropriate control sequences, the positioning and orientation of the coding sequence with respect to the control sequences being such that the coding sequence can be transcribed under the control of the regulatory sequences (i.e., by RNA polymerase which attached to the DNA molecule at the control sequences) in a host cell transformed by the expression cassette. It is possible to assemble the expression cassette prior to inserting it into a cloning vector as described above. Alternatively, an expression cassette can be constructed by cloning the coding sequence directly into an expression vector already containing the appropriate regulatory sequences and a restriction site downstream from the promoter.

Construction of expression vectors or expression cassettes for use in transforming microbial hosts (e.g., bacteria or yeast) may be desired to produce single-cell protein by fermentation to supplement the nutritive value of other protein sources. A number of prokaryotic expression vectors are known in the art which could be adapted for this purpose See, e.g., U.S. Pat. Nos. 4,440,859; 4,436,815; 4,431,740; 4,431,739; 4,428,941; 4,425,437; 4,418,149; 4,411,994; 4,366,246; 4,342,832. See also British Patent Nos. 2,121,054; 2,008,123; 2,007,675; and European Patent Pub. No. 103,395. Yeast expression vectors are also known in the art. See, e.g., U.S. Pat. Nos. 4,446,235; 4,443,539; 4,430,428; 4,546,082. See also European Patent Pub. Nos. 103,409; 100,561; 96,491.

A preferred class of heterologous hosts for the expression cassettes containing coding regions for arcelin are eukaryotic hosts, particularly the cells of higher plants (dicots, monocots). Particularly preferred among the higher plants are those of agronomic value having edible parts, such as leguminous plants, including, but not limited to, *Glycine max* (soybean), *Medicaqo sativa* (alfalfa), *Psophocarpus tetragonolobus* (winged bean), and *Vigna aconitifolia* (moth bean). Other bean cultivars, such as *P. vulgaris*, can be useful hosts. Crops in general, such as maize, may also be useful hosts.

Expression cassettes intended for use in higher plants will employ regulatory sequences functional in such plants. For example, promoters can be selected from the group consisting of plant promoters, plant virus promoters, and T-DNA promoters (from both Ti and Ri plasmids). Specific T-DNA promoters known in the art include the nopaline synthase (NOS) promoter, and the octopine synthase (OCS) promoter. These promoters are constitutive promoters. See, e.g., Plant Sciences (supra). Examples of plant virus promoters include the 19S and 35S transcript promoters from cauliflower mosaic virus (CaMV). See, e.g., Id.; Koziel et al. (1984) J. Mol. Appl. Genet. 2:549. Numerous plant promoters have been shown to work in heterologous systems, including, but not limited to, the pea small subunit RUBP carboxylase (pSS) promoter, Morelli et al. (1985) Nature (London) 315:200; Broglie et al. (1984) Science 224:838; Herrera-Estrella et al. (1984) Nature (London) 310:115; Coruzzi et al. (1984) EMBO J. 3:1671; the soybean small subunit RUBP carboxylase (SbSS) promoter, Facciotti et al. (1985) Bio/Technology 3:241; the maize zein promoter, Matzke et al. (1984) EMBO J. 3: 1525; the wheat chlorophyll a/b binding protein promoter, Lampa et al. (1985) Mol. Cell. Biol. 5:1370–1378; soybean 7S alpha, conglycinin promoter, Beachy et al. (1985) EMBO J. 4:3047; the soybean glycinin G2 promoter; soybean heat-shock promoter, EPO Publication No. 159,884; and the french bean phaseolin promoter, Sengupta-Gopalan et al. (1985) Proc. Natl. Acad. Sci. USA 82:3320; Murai et al. (1984) Science 222:476. Depending upon the application, it may be desirable to select from among the available promoters those which are tissue specific (e.g., seed, leave, etc.) and/or regulated (e.g., light-induced, temperature or heat-induced, developmentally regulated, etc.).

Particularly preferred promoters are those which allow for expression of arcelin in seeds of heterologous plants. Examples of such promoters include, but are not limited to, the phaseolin promoter and the soybean 7S alpha' conglycinin promoter. Expression cassettes intended for seed-specific expression can employ either heterologous promoters such as these, or the homologous promoter. In like manner, expression cassettes can employ heterologous signal peptides in a coding sequence, particularly those associated with the heterologous promoter, or arcelin's own signal peptide.

Various methods of transforming cells of higher plants with expression cassettes according to the present invention are available to those skilled in the art. See generally, Lichtenstein et al. in Genetic Engineering: Vol. 6, pp. 104–182 (Rigby ed. 1987). Among the most popular of transformation methods are those based on transformation vectors constructed of T-DNA from Ti or Ri plasmids. It is particularly preferred to use binary T-DNA vectors. See, e.g., Plant Sciences, supra. T-DNA based vectors have been shown to transform dicots and monocots, including, but not limited to, legumes (e.g., soybean, peas, and alfalfa), cotton, rape, tomato, Liliaceae (e.g., asparagus), Amaryllidaceae, etc. See, e.g., Plant Siences, supra, and references sited therein; Pacciotti et al. (1985) Bio/Technology 3:241; Byrne et al. (1987) Plant Cell, Tissue and Organ Culture 8:3; Sukhapinda et al. (1987) Plants Mol. Bio. 8:209–216; Lorz et al. (1984) Proceedings of EEC-Symp.: In Vitro Techniques-Propagation and Long-Term Storage; Lorz et al. (1985) Mol. Gen. Genet. 199:178; Potrykus et al. (1985) Mol. Gen. Genet. 199:183.

Other transformation methods are available to those skilled in the art. Viral transformation vectors are known, such as those based on CaMV. See, e.q., Brisson et al. (1984) Nature (London) 310:511; Gronenborn et al. (1981) Nature (London) 294:773. Transposons can also be used to transform plants, particularly monocots. Maize transposons include, for example, Ac and Ds transposons, as well as the Mul transposon. See, e.g., Plant Sciences, supra, at 28.

In the absence of a suitable transformation vector for desired higher plant host, such cells can be transformed by the direct uptake of DNA including expression cassettes of the present invention. The uptake of foreign DNA in plant cells using various chemical agents is known. See, e.g., Davey et al. (1980) Plant Sci. Lett. 18:307; Draper et al. (1982) Plant Cell Physiol. 23:1; Krens et al. (1982) Nature (London) 296:72; Hain et al. (1985) Mol. Gen. Genet. 199:161; Hooykaas-van Slogteren et al. (1984) Nature (London) 311:763; Hernalsteens et al. (1985) EMBO J. 3:3039. Higher plant protoplasts have also been transformed by techniques of electroporation. See, e.g., Fromm et al (1986) Nature (London) 319:791; Fromm et al. (1985) Proc. Natl. Acad. Sci. USA 82:5824; Potter et al. (1984) Proc. Natl. Acad. Sci. USA 81:7161. Plant cells may also be transformed with foreign DNA by micro-injection using known techniques, or by high-velocity metal particles coated with RNA or DNA. See, e.g., Kline et al. (1987) Nature (London) 327:70.

Once transformed plant cells have been produced, it is usually desirable to grow transformed cells into callous tissue or a cell line in suspension. Techniques for regenerating callous and for producing cell lines are known in the art. See, e.g., Plant Cell Culture, supra; Propagation of Higher Plants Through Tissue Culture, supra. Transformed cells can also be induced to undergo organogenesis. Thus, transformed cells can be maintained as undifferentiated tissues, or in organ culture. These plant cell cultures or organ cultures can be used, therefore, to produce arcelin. See, e.g., Flores in Biotechnology and Agricultural Chemistry; ASC Symposium Series 334, p.66 (LeBaron et al. eds., 1987).

Another important application of the present invention is the production of plants transformed with the coding sequences for arcelin. Techniques for regenerating plants from tissue culture, such as transformed protoplasts or callous cell lines, are known in the art. See, e.g., Bingham et al. (1975) Crop Sci. 15:719–721; Kao et al. (1980) Z. Pflanzenphysiol Bd. 96:135–141; Reisch et al. (1980) Plant Sci. Lett. 20:71–77; U.S. Pat. No. 4,548,901; Wright et al. (1987) Plant Cell Rpts. 6:83; Christianson et al. (1983) Science 222:632; Hammatt et al. (1987) Plant Science 48:129; Ghazi et al. (1986) Plant Cell Rpts. 5:452; Barwale et al. 1986) Planta 167:473; Newell et al. (1985) Plant Cell Tissue Organ Culture 4:145; Phillips et al. (1981) Plant Cell Tissue Organ Culture 1:123; Eapen et al. (1986) Theor. Appl. Genet. 72:384; Krishnamurthy et al. (1984) Plant Cell Rpts. 3:30; Shekhawat et al. (1983) Plant Sci. Lett. 32:43; Wilson et al. (1985) Plant Sci. 41:61; Venstesnaran et al. (1985) In Vitro 21(3,II): 36A. The selection of an appropriate method is within the skill of the art.

Set forth below are specific examples of the present invention which are intended for illustrative purposes only. These examples are not intended to limit the present invention in any manner. The references cited herein are incorporated by reference.

EXAMPLES

I. Characterization of Arcelin

A. Materials and Methods

Plant Materials. Three near-isogenic lines of *Phaseolus vulgaris* with different seed protein compositions were used for this study. 'Sanilac' is a navy bean cultivar that contains both phaseolin and PHA seed proteins, but no arcelin. L12≧56 is a line developed by backcrossing the allele for PHA deficiency into 'Sanilac' (Osborn et al., 1985, J. Am. Soc. Hort. Sci. 110: 484–488), and therefore contains phaseolin but no detectable PHA or arcelin. Line, SARC1-7, containing phaseolin, PHA and arcelin, was developed by backcrossing the arcelin-1 allele and the tightly linked PHA locus from the wild bean line, UW325 (Romero Andreas et al., 1986, supra) into Sanilac.

Protein purification. Arcelin, PHA and phaseolin seed proteins were purified from seed of SARC1-7. Bean flour (10 g) was stirred in 100 ml of 10 mM NaCl (pH2.4) for 1 h at room temperature, then the mixture was centrifuged (30,000 g, 20 min, at 4° C.). The pellet was re-extracted and centrifuged as above and the residual pellet was saved for phaseolin extraction. The supernatants were combined (180 ml) and dialyzed for 24 h at 4° C. against three changes of 6 l dH$_2$O. The precipitate (globulin-a) was pelleted by centrifugation and the globulin-a and supernatant (albumin-a) were lyophilized. Globulin-a (50 mg) was dissolved in 10 mM NaCl (pH 2.4), centrifuged and the supernatant was dialyzed against dH$_2$O as before.

The protein that precipitated after dialysis (globulin-b) was pelleted by centrifugation and the globulin-b and supernatant (albumin-b) were lyophilized. PHA was removed from the albumin-b fraction by Sepharose-thyroglobulin or Sepharose-fetuin affinity chromatography. Osborn et al. (1983) Plant Sci. Lett. 31:193–203. The protein that did not bind to the affinity ligand was shown electrophoretically to be highly purified arcelin. PHA bound to the affinity ligand and after extensive washing with PBS, it was eluted with 0.5M NaCl containing 0.1M glycine (pH 3.0). The arcelin and PHA were dialyzed against ddH$_2$O and lyophilized.

Phaseolin was extracted from the residual pellet by stirring in 0.5M NaCl (pH 2.4) for 30 min at room temperature. This mixture was centrifuged and the supernatant was dialyzed at 4° C. against dH20. The precipitant was pelleted by centrifugation, washed with cold ddH$_2$O, redissolved in 0.5M NaCl, centrifuged and the supernatant was dialyzed at 420 C. against dH2O. This was repeated twice and the final pellet (phaseolin) was lyophilized. Protein samples were dissolved in PBS, except phaseolin which was dissolved in 0.5M NaCl, for electrophoresis and hemagglutination assays.

Electrophoresis. Protein samples were mixed with an equal volume of cracking buffer (0.625M Tris-HCl (pH 6.8), 2 mM EDTA, 2% (w/v) SDS, 40% (w/v) sucrose, 1% (v/v) B-mercaptoethanol, 0.01% (w/v) bromophenol blue) and placed in a boiling water bath for 5 min. Proteins were separated by SDS-PAGE in 15% polyacrylamide slab gels. Laemmli (1970) Nature 227:680–685; Ma et al. (1978) Crop Sci. 17:431–437. Gels were stained with Coomassie brilliant blue brilliant blue R250 (1.5% (w/v) in 45% (w/v) ethanol and 9% (w/v) acetic acid) and destained with a solution of 20% (w/v) ethanol, 6% (w/v) acetic acid. The $M_r$ values of denatured and deglycosylated arcelin and PHA were calculated from comparisons to the electrophoretic mobilities of standard proteins. The isoelectric point of purified arcelin was determined by isoelectric focusing in polyacrylamide tube gels containing 8M urea. O'Farrell (1975) J. Biol. Chem. 250:4007–4021. The ampholines used, pH 5–8 (LKB) and pH 3–10 (BioRad), generated a pH gradient of 4.5 to 7.8 as determined by measuring the pH of 0.5 cm gel slices after soaking in 1M KCl for 3 h.

Gel Filtration. The $M_r$ of native arcelin and PHA proteins were determined by filtration through a Sephacryl S-300 (Pharmacia) column (1.5×118 cm) with a flow rate of 6.45 ml/hr and monitoring the absorbance of the effluent at 280 nm. PBS was used as the equilibration, elution and sample dissolving buffer.

Deglycosylation and Detection of Glycoproteins. Purified arcelin and PHA were chemically deglycosylated using trifluoromethane sulfonic acid. Edge et al. (1981) Anal. Biochem. 118:131–137. Arcelin was treated in the acid solution for 1 h at room temperature and PHA was treated for 3 h at 4° C. Deglycosylated samples were lyophilized and dissolved in cracking buffer for SDS-PAGE. After SDS-PAGE, gels were fixed with a solution of 5% (v/v) formaldehyde and 25% (v/v) ethanol. Gels were rinsed twice in 50% (v/v) methanol and twice in dH2 O and then successively treated with paraperiodic acid, sodium metabisulfite, acidic dimethylsulfoxide, and dansyl hydrazine. Eckhardt et al. (1976) Anal. Biochem. 73:192–197. Carbohydrates were visualized and photographed under Uv light. A control gel, omitting the paraperiodate oxidation, was included and showed no detectable staining.

Amino Acid and Sugar Analysis. Purified arcelin was analyzed for amino acid composition by Allan Smith, University of California, Davis. All amino acids, except cysteine and tryptophan, were separated using a Durrum D-500 amino acid analyzer after a 24 h hydrolysis in 6N HCl at 110° C. under nitrogen. Cysteine was determined as cysteic acid after performate oxidation. Tryptophan was quantified by the acid-ninhydrin method (Gaitonde et al., 1970, Biochem. J. 117:907–911) and compared to the protein content as estimated by the biuret method . Gornall et al. (1949) J. Biol. Chem. 177:751–766. Glucosamine and galactosamine were estimated by extrapolating to time zero the values obtained on a Beckman 6300 amino acid analyzer after 4 and 6 h hydrolysis in 4N HCl at 100° C. Neutral sugars were estimated by the phenol-sulfuric acid method using mannose as standard. Dubois et al. (1956) Anal. Chem. 28:350–356.

Cyanogen Bromide Cleavage. Purified arcelin was cleaved into peptides using cyanogen bromide as described previously (Gross et al., 1962, J. Biol. Chem. 237:1856–1860) except that 72% (v/v) formic acid was used instead of 0.1N HCl. The reaction was stopped after 20 h by freezing at −80° C., followed by lyophilization. Digestion products were separated by SDS-PAGE using Tris-borate as running buffer. Francis et al. (1984) J. Chromatogr. 298:115–121. After electrophoresis, the gel was formaldehyde-fixed and stained with Coomassie brilliant blue R-250. Steck et al. (1980) Anal. Biochem. 107:21–24.

Hemagglutination Assays. The hemagglutinating activities of purified proteins and crude bean extracts were determined using erythrocytes from rabbit, mouse, human type A, guinea pig, rat and cow blood. Erythrocytes were prepared as described previously (Brown et al., 1982, Theor. Appl. Genet. 62:263–271) using the same procedure to treat cells with pronase as was described for the trypsin treatment of cells.. Crude protein extracts were obtained by stirring bean flour in PBS (2% w/v) for 1 h at room temperature followed by centrifugation (12,000g, 4° C., 20 min). Crude extracts and purified proteins (2mg/ml) were serially diluted with equal volumes of PBS and 50 ul of each dilution step was mixed with 50 ul of native or treated erythrocytes (3% v/v in PBS) in wells of micro-titre plates. Hemagglutinating activity was scored visually after 1 h at room temperature.

Immunoblotting. Rabbit antibodies were raised against purified arcelin by injecting subcutaneously 100 ug of arcelin with Freund's complete adjuvant, followed four weeks later with a second injection containing 100 ug arcelin and Freund's incomplete adjuvant and a third injection one week later. The rabbit was bled three days after the last injection and the serum frozen. Mouse serum containing antibodies to deglycosylated PHA was kindly provided by Leslie Hoffman, Agrigenetics Corporation, Madison, Wis. Immunoblotting of proteins separated by SDS-PAGE was performed as described previously (Vierstra et al., 1985, J. Biol. Chem. 260:12015-12021) except that the blocking solution was 1% (w/v) BSA, 5% (w/v) non-fat dried milk, 20 mM Tris-HCl (pH 7.5) and 0.15M NaCl. Primary antiserum was used in a 1/500 dilution in the blocking solution and secondary antibody was either goat anti-rabbit or rabbit anti-mouse immunoglobin G conjugated to alkaline phosphatase (Sigma) (1 ul/ml blocking solution). Proteins were visualized colorimetrically using the phosphatase substrates nitroblue tetrazolium and 5-bromo-4-chloro-3-indolyl phosphate. Vierstra et al., supra. A control immunoblot treated with rabbit preimmune sera showed no detectable reaction.

Developmental Study. Developing seeds of Sanilac, L12-56 and SARC1-7 bean lines were harvested from greenhouse plants grown under natural light beginning 10 days after flowering up until pod maturity (36 days after flowering). Seeds were frozen in liquid nitrogen and stored at $-80°$ C. Cotyledons from each sample were ground in 0.5 M NaCl, 50 mM sodium phosphate (pH 7.2) (10% w/v) using a mortar and pestle. One ml of mixture was centrifuged and the supernatant was stored at $-80°$ C. The samples were diluted with an equal volume of 0.5M NaCl (three volumes for mature seeds) and separated by SDS-PAGE.

B. Results

Protein Purification. Three major protein fractions, arcelin, PHA and phaseolin, were purified from seed of SARC1-7 using differential solubility properties and affinity chromatography. These purified proteins, along with various intermediate fractions from the purification procedure, were separated by SDS-PAGE. The initial low salt extract (10 mM NaCl, pH 2.4) contained very little phaseolin as compared to a high salt extract (0.5M NaCl). Arcelin proteins were present in both the globulin-a and albumin-a fractions derived from the low salt extract. When the globulin-a pellet was redissolved in low salt buffer and dialyzed against dH2O, some arcelin precipitated with the globulin-b fraction; however a highly purified arcelin protein remained soluble in the albumin-b fraction. A small amount of PHA present in the albumin-b fraction was removed by affinity chromatography yielding purified arcelin. Phaseolin was purified from the pellet of the initial flour extraction.

Glycosylated and Deglycosylated Proteins. Arcelin and PHA are both glycosylated proteins as demonstrated by carbohydrate-staining with dansyl hydrazine. When chemically deglycosylated, arcelin yielded a single polypeptide and PHA yielded two polypeptides. The deglycosylated proteins showed no carbohydrate-staining with dansyl hydrazine.

Molecular Weights and Isoelectric Points. The molecular weights of native, denatured and deglycosylated arcelin-1 and PHA, and the isoelectric points of these proteins are reported in Table I. The denatured arcelin protein contained a major polypeptide of $M_r$ 37,400 and a minor polypeptide of $M_r$ 35,800. A second minor polypeptide having an intermediate $M_r$ sometimes could be resolved by SDS-PAGE. Two-dimensional isoelectric focusing/SDS-PAGE of purified arcelin also showed one major and two minor polypeptides, all of which had similar electrophoretic mobilities. The denatured PHA protein contained a major polypeptide of $M_r$ 34,300 and several minor polypeptides with $M_r$'s ranging from 32,700 to 40,700. The deglycosylated forms of arcelin and PHA had very similar $M_r$ values ranging from 29,000 to 30,800. The isoelectric points of arcelin and PHA were significantly different; arcelin focused at two pH values, 6.7 and 6.8; whereas PHA focused in the range of pH 5.2 to 5.4.

The molecular weights of native proteins were determined by gel filtration. PHA eluted as a single peak with a $M_r$ of 146,100, corresponding to a tetramer of polypeptide subunits. The native arcelin protein eluted as a minor peak with $M_r$ of 159,600 and a major peak with $M_r$ of 80,900, corresponding to the tetramer and dimer of polypeptide subunits, respectively. Polypeptide components of these two native forms had different electrophoretic mobilities. The tetrameric peak consisted of the higher $M_r$ minor polypeptide, and the dimeric peak consisted of the major 37,400 $M_r$ subunit and the lower $M_r$ minor subunit. A third, minor peak contained no protein visible by Coomassie blue staining.

TABLE I

Relative molecular weights ($M_r$) and isoelectric points of purified arcelin and PHA.

| | Bean Seed Protein | |
|---|---|---|
| | Arcelin | PHA |
| $M_r$ native | 80,900; 159,600 | 146,100 |
| $M_r$ denatured | 35,800–37,400 | 32,700–40,700 |
| $M_r$ deglycosylated | 29,900 | 29,000; 30,800 |
| Isoelectric point (pH) | 6.7; 6.8 | 5.2–5.4 |

Chemical Compositions. The results of amino acid and sugar analyses of arcelin together with the published analyses of PHA and phaseolin are shown in Table II. The amino acid compositions of all three proteins had some similarities; however, those of arcelin and PHA were more similar to each other than to the composition of phaseolin. Arcelin differed from PHA in that it contained some methionine (<1 residue/subunit), more cysteine and more basic amino acid residues than did PHA. Arcelin also contained more sugar residues than either PHA or phaseolin, and based on the percentage neutral sugars and glucosamine, the predicted deglycosylated molecular weight of arcelin (29,900 Daltons) agreed exactly with the $M_r$ of the deglycosylated arcelin.

The presence of at least one methionine residue in the arcelin protein also was detected by cyanogen bromide cleavage. The primary cleavage product had a $M_r$ of 32,000. A minor cleavage product ($M_r$=29,000) also was observed which probably corresponded to a cleavage product from the minor arcelin polypeptide ($M_r$=35,800). If arcelin protein has a single methionine residue, cleavage products of approximately 5,000 Daltons would also be expected.

TABLE II

Chemical Composition of Major Bean Seed Storage Proteins

| Amino Acid | mole percent amino acids | | |
|---|---|---|---|
| | Arcelin | PHA[a] | Phaseolin[b] |
| Asx | 14.9 | 12.5 | 11.9 |
| Thr | 7.3 | 9.6 | 4.2 |
| Ser | 11.5 | 14.4 | 9.4 |
| Glx | 8.2 | 6.7 | 15.2 |
| Pro | 3.3 | 3.1 | 3.7 |
| Gly | 5.7 | 6.8 | 5.2 |
| Ala | 6.1 | 6.6 | 4.9 |
| Cys | 1.1 | 0.2 | 0.3 |
| Val | 7.1 | 7.7 | 6.5 |
| Met | 0.2 | 0.0 | 0.7 |
| Ile | 4.7 | 5.4 | 6.3 |
| Leu | 6.7 | 8.9 | 10.2 |
| Tyr | 3.0 | 2.3 | 2.8 |
| Phe | 6.5 | 5.7 | 5.9 |
| Lys | 5.9 | 4.7 | 5.6 |
| His | 2.4 | 1.1 | 2.5 |
| Arg | 4.7 | 2.4 | 4.3 |
| Trp | 0.9 | 2.0 | 0.6 |
| | g/100 g glycoprotein | | |
| Neutral sugars | 16.9 | 9.1 | 4.5 |
| Glucosamine | 3.7 | 1.4[c] | 1.0 |
| Galactosamine | 0.0 | — | — |

[a]Moreira et al. (1977) Plant Physiol. 59:783-787.
[b]Pusztai et. al. (1970) Biochem. Biophys. Acta 207:413-431.
[c]Total amino sugars.

contained mostly arcelin and a small amount of PHA. Arcelin protein (purified from albumin-b by removing PHA) did not agglutinate any of the native erythrocytes, but had strong agglutinating activity with pronase-treated rabbit, mouse and human cells and weak activity with pronase-treated rat and cow cells and trypsin-treated cow cells. No hemagglutinating activity was observed for purified phaseolin.

The observed hemagglutinating activity of purified arcelin could have been due to a small amount of PHA contamination. To test this possibility, purified arcelin was passed a second time through the Sepharosethyroglobulin affinity resin and retested for hemagglutinating activity (arcelin, 2nd pass). There was no significant reduction in agglutinating activity for the cells tested, indicating that the observed activity was not due to PHA contamination. The ability of arcelin to agglutinate some treated cells also can be inferred by comparing the SARC1-7 crude extracts and purified PHA for their relative activity with native and pronase-treated cells. Some component of the SARC1-7 crude extract (i.e., arcelin) is responsible for a greater activity with pronase-treated versus native rabbit, mouse and human cells than was observed for purified PHA. The relative differences between native and pronase-treated guinea pig cells, which did not react with arcelin, were the same for SARC1-7 crude extract and PHA.

TABLE III

Agglutinating Activity[a] of Crude Bean Seed Extracts and Purified Proteins with Erythrocytes from Different Animal Sources

| | Erythrocyte Source | | | | | | | | | | | |
|---|---|---|---|---|---|---|---|---|---|---|---|---|
| | Rabbit | | Mouse | | Human | | Guinea Pig | | Rat | | Cow | | |
| Sample | N | P | N | P | N | P | N | P | N | P | N | P | T |
| Crude Extracts | | | | | | | | | | | | | |
| L12-56 | 0 | 0 | 0 | 0 | 0 | 0 | 0 | 2 | 0 | nd | 0 | 2 | 1 |
| Sanilac | 8 | 10 | 7 | 12 | 8 | 12 | 9 | 10 | 6 | ≧3 | 0 | 5 | 6 |
| SARC1-7 | 7 | 10 | 6 | 12 | 6 | 13 | 7 | 8 | 5 | nd | 0 | 8 | 9 |
| Purified Protein | | | | | | | | | | | | | |
| PHA | 9 | 10 | 9 | 12 | 8 | 12 | 9 | 10 | 7 | ≧3 | 0 | 10 | 11 |
| Albumin-b | 3 | 7 | nd | 8 | 2 | 10 | 4 | nd | nd | nd | 0 | nd | 8 |
| Arcelin | 0 | 5 | 0 | 7 | 0 | 8 | 0 | 0 | 0 | 1 | 0 | 1 | 2 |
| Phaseolin | 0 | 0 | 0 | 0 | 0 | 0 | 0 | 0 | nd | 0 | 0 | 0 | 0 |
| Arcelin, 2nd pass | 0 | 5 | nd | nd | 0 | 7 | 0 | nd | nd | nd | 0 | nd | 2 |

[a]Numbers indicate last dilution step with hemagglutinating activity (higher number indicates more activity; 0 = no hemagglutinating activity observed; nd = not determined).
$b_N$ = native erythrocytes;
P = pronase-treated erythrocytes;
T = trypsin-treated erythrocytes.

Hemagglutinin Assays. The hemagglutinating activities of crude and purified proteins are shown in Table III. Erythrocytes treated with pronase or trypsin were more sensitive to agglutination as has been reported for purified PHA (Pardeo et al., 1970, Z. Immun-Forsch Bd. 140:374-394) and crude bean extracts (Jaffe et al., 1972, Z. Immun-Forsch Bd. 142:439-447). Crude extracts of L12-56, which lacks acrelin and PHA, had very low agglutinating activities with only two cell types treated with pronase or trypsin. The crude extract of Sanilac, which contains PHA, had high levels of activity for all native and treated erythrocytes tested, except for native cow cells. This was also observed for the SARC1-7 extract, which contained arcelin and small quantities of PHA. PHA protein purified from SARC1-7 had strong agglutination activity with both native and pronase- or trypsin-treated cells and activity also was observed in the albumin-b fraction, which Immunoblots. Immunoblot analyses of crude and purified proteins using antibodies against purified arcelin were performed. These antibodies reacted strongly with purified arcelin and with arcelin in the crude extract. Two lower molecular weight proteins in the crude extract also bound arcelin antibody. These proteins were removed during arcelin purification; however, they were observed previously to co-segregate with arcelin protein in $F_2$ progenies and may represent low molecular weight arcelin proteins. Arcelin antibodies also cross-reacted with purified PHA and PHA in the crude Sanilac extract, but did not react with L12-56 crude extract or with purified phaseolin.

The observed antibody cross-reaction may have been due to antigenic similarities in carbohydrate groups rather than similarities in protein structure. Therefore, immunoblots were tested using antibodies raised against deglycosylated PHA. These antibodies reacted strongly with purified PHA and PHA in the 'Sanilac' and SARC1-7 extracts. There was also cross-reaction with purified arcelin and with one of the low molecular weight proteins in the SARC1-7 extract. These antibodies weakly bound a protein in the L12-56 extract which also appeared to be present in the SARC1-7 extract. This protein may represent the low-abundance lectin isolated from PHA-deficient 'Pinto UI 111' seeds Pusztai et al. (1981) Biochem. Biophys. Acta 671:146–154.

Developmental Accumulation. The accumulation of arcelin, PHA and phaseolin proteins was studied using developing seeds of the three near-isogenic backcross lines: L12-56 (containing phaseolin). Sanilac (containing phaseolin and PHA) and SARC1-7 (containing phaseolin, PHA and arcelin). Proteins extracted from seeds at each developmental stage were separated by SDS-PAGE. In the L12-56 line, most of the phaseolin accumulated between 12 and 24 days after flowering. A similar accumulation profile was observed for both phaseolin and PHA proteins in Sanilac. In the SARC1-7 line, phaseolin accumulated between 12 and 20 days after flowering, whereas most of the arcelin protein accumulated between 12 and 24 days after flowering.

II. Pest Resistance

Backcrossing. Although the presence of arcelin is correlated with bruchid resistance in wild beans, factors other than arcelin protein might confer the resistance property. To test whether resistance is associated with the genetic transfer of arcelin, we introduced the arcelin-1 allele from the wild line, UW325 (Example I) into the bean cultivar Sanilac (Example I), by two generations of backcrossing followed by two selfing generations. The expression of arcelin is controlled by a single Mendelian gene and the presence of arcelin is dominant to absence.

Seeds of backcross lines were tested for resistance to *Z. subfasciatus* (Table IV). Lines were screened for resistance as described previously. Schoonhoven et al. (1982) J. Econ. Entomol. 75:567. Values in the table represent the mean (± SEM) of two replicates containing 50 seeds each, each replication infested with 7 insect pairs. Based on percentage emergence of adults and life cycle duration of larvae, all arcelin-1-containing lines showed high levels of resistance. Lines lacking arcelin-1 were fully susceptible compared to the check cultivar, and lines segregating for arcelin-1 had intermediate levels of resistance. These results demonstrate that the arcelin-1 variant is associated with high levels of resistance to *Z. subfasciatus*. They also indicate that resistance is associated with the genetic transfer of arcelin-1 expression.

Analogous sets of backcross lines were developed using different cultivated bean types (e.g. the black-seeded cv. Porrillo) as recurrent parents. These lines were tested for resistance to *Z. subfasciatus* and similar results were obtained. The backcross lines also were tested for resistance to *A. obtectus*, but in this case only low levels of resistance were associated with the presence of arcelin-1. Resistance of Sanilac backcross-derived lines was tested using two replicates of 50 seeds each as described in Schoonhoven et al. (1983) J. Econ. Entomol. 76:1255. The mean of backcross lines for numbers of days until adult emergence and for percentages emergence were 39.6 (±0.4) and 31.5 (±1.4), respectively, for arcelin-1 containing lines, and 35.6 (±0.7) and 51.7 (±5.0), respectively, for backcross lines without arcelin-1. The resistance to *Z. subfasciatus* is due to larval antibiosis (up to 97% mortality of first instar larvae) and could be caused by the arcelin protein or by some factor that is linked genetically to arcelin expression.

TABLE IV

Levels of resistance to *Z. subfasciatus* in Sanilac backcross-derived lines with arcelin-1 ($Arc^1/Arc^1$), without arcelin-1 (Arc/Arc) and segregating for arcelin-1 (Arc1/Arc)

| Line or cultivar | Arcelin genotype | No. of days until adult emergence | Percentage emergence |
|---|---|---|---|
| Backcross line | | | |
| 3 | $Arc^1/Arc^1$ | 53.0 (±1.0) | 2.5 (±0.4) |
| 5 | $Arc^1/Arc^1$ | 47.8 (±4.5) | 2.1 (±0.3) |
| 4 | $Arc^1$/arc | 33.2 (±3.3) | 20.9 (±7.9) |
| 7 | $Arc^1$/arc | 37.2 | 38.7 |
| 8 | $Arc^1$/arc | 38.1 | 34.6 |
| 9 | $Arc^1$/arc | 35.4 | 30.2 |
| 1 | arc/arc | 34.2 (±0.2) | 89.5 (±5.4) |
| 2 | arc/arc | 34.7 (±0.1) | 76.3 (±2.1) |
| 6 | arc/arc | 34.4 (±0.4) | 93.8 (±8.8) |
| Susceptible cultivar | | | |
| Calima | arc/arc | 34.0 (±0.4) | 92.9 (±5.4) |

Artificial Seeds. To determine whether or not arcelin protein is the factor conferring bruchid resistance, we produced artificial bean seeds containing various levels of purified arcelin-1 and tested these seeds for resistance to *Z. subfasciatus* (Table v) using the system devised for cowpea weevil. Shade et al. (1986) Environ. Entomol. 15:1286. The values in the table represent the mean (± SD) of four replicates containing five seeds each. In this test, we included intact seeds from four cultivated bean lines. 'Calima', Sanilac (which contains PHA), and L12-56 (a backcross line near-isogenic to Sanilac but which is PHA-deficient, Osborne et al., 1985, supra), were all susceptible to bruchid infestation, whereas SARC1-7, a Sanilac backcross-derived line homozygous for the presence of arcelin-1, was resistant.

These results indicate that the presence or absence of PHA does not affect bruchid development, but as noted before, arcelin-1 is associated with a high level of resistance. After soaking and removal of the seed coat, seeds of these lines were ground into flour, reconstituted as 'artificial' seeds (Shade et al., supra) and tested for bruchid resistance. Although the absolute values for larval life cycle duration and percentage emergence were different than for intact seeds, resistant and susceptible responses were easily distinguished.

Artificial seeds consisting of Sanilac flour to which purified arcelin-1 (Example I) was added at three different levels were tested for resistance. The approximate amount of arcelin-1 in seeds was determined by extracting bean flour with cracking buffer, or dissolving purified acrelin-1 in the same buffer, then separating seed proteins by SDS/PAGE (Osborn et al., 1986, supra), and scanning the coomassie-stained gel with a densitometer. By comparison with known amounts of purified acrelin run on the same gel, the acrelin protein was estimated to be 10% (w/w) of SARC1-7 bean flour. The highest level of arcelin-1 in an artificial seed (10% w/w) represents the approximate concentration of arcelin in seed of SARC1-7 and the lower levels, 5% and 2.5% w/w, represent approximately one-half and onequarter, respectively, of the arcelin concentration present in SARC1-7.

At the lowest level tested, arcelin had no significant antibiosis effect on larvae. At the intermediate arcelin level, there was a significant increase in the larval life cycle duration but no significant effect on percentage emergence. However, the response of insects to the highest level of arcelin was nearly identical to that of insects reared on artificial seeds of SARC1-7 for both measures of resistance. This indicates that the presence of arcelin-1 in bean seeds confers resistance to *Z. subfasciatus*. The dosage response of larvae as measured by life cycle duration was nearly linear over the range of arcelin levels tested. For percentage emergence, a significant dosage response was observed only at the highest arcelin level, indicating that high levels are needed to affect this parameter.

TABLE V

Levels of resistance to *Z. subfasciatus* in intact and 'artificial' bean seeds with and without the addition of purified arcelin-1

| Material screened | No. of days until adult emergence | Percentage emergence |
|---|---|---|
| Intact seed | | |
| L12-56 | 32.2 (±0.6) | 100.0 (±0) |
| Sanilac | 31.3 (±0.6) | 95.9 (±4.9) |
| SARC1-7 | 50.3 (±3.5) | 7.4 (±7.4) |
| Calima | 31.5 (±0.5) | 93.0 (±5.7) |
| Artificial seed | | |
| L12-56 | 38.4 (±1.5) | 74.7 (±18.7) |
| Sanilac | 37.8 (±2.0) | 86.1 (±5.9) |
| SARC1-7 | 53.8 (±2.3) | 18.4 (±14.7) |
| Calima | 37.9 (±0.6) | 87.7 (±13.6) |
| Sanilac + 2.5% arcelin-1 | 38.9 (±1.6) | 76.1 (+11.8) |
| Sanilac + 5.0% arcelin-1 | 44.7 (±1.7) | 76.1 (±19.5) |
| Sanilac + 10.0% arcelin-1 | 53.4 (±3.5) | 18.4 (±17.6) |

III. Cloning of Arcelin DNA Sequence

The following example provides a protocol for cloning arcelin-encoding DNA sequences, such as cDNAs.

Developing bean seeds of SARC1-7 were harvested 13-19 days after flouring and mRNA was isolated using the procedure described in Hall et al. (1978) *Proc. Natl. Acad. Sci. USA* 75:3196, except that the sucrose gradient centrifugations were omitted. The mRNA was used to construct a cDNA library in the pARC7 cDNA cloning vector. Alexander et al. (1984) *Gene* 31:79.

Candidate clones for arcelin-1 were selected by differential hybridization of colony lifts. Filters were prepared according to Taub et al. (1982) *Anal. Biochem.* 126:222. Filters were probed sequentially with three different probes. The probes, which were $^{32}$P-labeled cDNA first strands made from mRNA fractions of developing seeds, were from (i) L12-56, a lectin-deficient bean line with phaseolin as the only major seed protein, (ii) the cultivar Sanilac, which contains PHA as well as phaseolin, and (iii) SARC1-7, which contains phaseolin, PHA, and arcelin-1. Arcelin cDNA candidates were selected as those colonies which were heavily labeled with SARC1-7 cDNA, but not by the other two cDNAs.

The nucleotide sequence (Sanger et al., 1978, *FEBS Lett.* 87:107) of candidate clone pAR1-11 contained multiple potential initiation sites near the 5' end of the clone, two of which were in the same large open reading frame encoding 269 amino acids (FIG. 1). Initiation at the third ATG would yield a 265 amino acid polypeptide. Comparison of this derived amino acid sequence to the N-terminal amino acid sequence of purified arcelin-1 protein demonstrated that pAR1-11 encodes arcelin-1. The mature protein sequence, which begins at codon 22 of the 265 amino acid open reading frame, matches the predicted sequence exactly through 47 of 48 amino acids determined by Edman degradation sequencing; amino acid residue number 12 yielded a blank by protein sequencing, presumably because of glycosylation of this predicted asparagine residue. The 21 residue peptide not found in the mature protein has the properties of a classic 'signal' peptide.

A clone of pAR1-11 in *E. coli* has been deposited with the American Type Culture Collection (ATCC), 12301 Parklawn Drive, Rockville, Md. 20852 USA. This deposit will be maintained under the terms of the Budapest Treaty.

Variations on the above embodiments are within the ability of one of ordinary skill in the art, and such variations do not depart from the scope of the present invention as described in the following claims.

We claim:

1. A composition comprising DNA molecules containing a coding sequence encoding arcelin-1 or an allelic variant thereof, said composition being substantially free of DNA molecules that do not contain said coding sequence.

2. A composition according to claim 1 wherein said DNA molecules are replicons.

3. A DNA molecule containing a coding sequence encoding arcelin-1 or an allelic variant thereof wherein said coding sequence is flanked by heterologous sequences which are T-DNA.

4. A DNA molecule containing a coding sequence encoding arcelin-1 or an allelic variant thereof wherein said coding sequence is flanked by heterologous sequences which are plant virus nucleic acid sequences.

5. A plant cell comprising a DNA sequence according to claim 3.

6. A plant cell comprising a DNA sequence according to claim 4.

7. A recombinant DNA sequence containing an expression cassette, said cassette containing a coding sequence encoding arcelin-1 or an allelic variant thereof, said coding sequence being under the transcriptional and/or translational control of regulatory sequences which are heterologous to said arcelin-encoding DNA.

8. A composition of cloning vectors, wherein each cloning vector in said composition contains a segment of DNA encoding arcelin-1 or the allelic variants thereof.

9. The recombinant DNA sequence of claim 7 wherein the control sequences of the expression cassette include a promoter selected from the group consisting of the nopaline synthase promoter, the octopine synthase promoter, the pea small subuit RUBP carboxylase promoter, and the soybean small subunit RUBP carboxylase promoter, the maize zein promoter, the wheat chlorophyll A/B binding protein promoter, soybean 7S-alpha'-conglycinin promoter, the soybean glycinin G2 promoter, soybean heat shock promoter, and the french bean phaseolin promoter.

10. A plant cell comprising the recombinant DNA sequence of claim 7.

11. A plant cell comprising the recombinant DNA sequence of claim 9.

12. A plant cell which has been transformed with the recombinant DNA sequence of claim 7.

13. A plant cell which has been transformed with the recombinant DNA sequence of claim 9.

14. A plant comprising the recombinant DNA sequence of claim 7.

15. A plant comprising the recombinant DNA sequence of claim 9.

16. A plant regenerated from the cells of claim 12 or the progeny of said plant.

17. A plant regenerated from the cells of claim 13 or the progeny of said plant.

* * * * *